(12) United States Patent
Rehe

(10) Patent No.: US 10,831,020 B2
(45) Date of Patent: Nov. 10, 2020

(54) OPTICAL SYSTEM FOR AN ENDOSCOPE

(71) Applicant: Henke-Sass, Wolf GmbH, Tuttlingen (DE)

(72) Inventor: Oliver Rehe, Wurmlingen (DE)

(73) Assignee: Henke-Sass, Wolf GmbH, Tuttlingen (DE)

( * ) Notice: Subject to any disclaimer, the term of this patent is extended or adjusted under 35 U.S.C. 154(b) by 524 days.

(21) Appl. No.: 15/482,736

(22) Filed: Apr. 8, 2017

(65) Prior Publication Data

US 2017/0293139 A1    Oct. 12, 2017

(30) Foreign Application Priority Data

Apr. 8, 2016    (DE) .................... 10 2016 106 518

(51) Int. Cl.
*G02B 23/24* (2006.01)
*G02B 21/02* (2006.01)
(Continued)

(52) U.S. Cl.
CPC ...... *G02B 27/0025* (2013.01); *A61B 1/00126* (2013.01); *A61B 1/00128* (2013.01);
(Continued)

(58) Field of Classification Search
CPC ...... G02B 3/02–04; G02B 13/001–002; G02B 13/008; G02B 13/0095;
(Continued)

(56) References Cited

U.S. PATENT DOCUMENTS 5,142,410 A * 8/1992 Ono .................... G02B 23/2446
359/434
6,088,157 A * 7/2000 Mazurkewitz ..... G02B 23/2446
359/434

(Continued)

FOREIGN PATENT DOCUMENTS

CN    104905759 A    9/2015
CN    105377113 A    3/2016
(Continued)

*Primary Examiner* — Thong Q Nguyen
(74) *Attorney, Agent, or Firm* — Skaar Ulbrich Macari, P.A.

(57) ABSTRACT

An optical system for an endoscope includes an objective and a reversal system arranged after the objective. The reversal system includes at least one reversal stage for projecting the distal intermediate image as a proximal intermediate image into a proximal intermediate image plane. The reversal system imprints on the proximal intermediate image a first longitudinal chromatic aberration referred to a predetermined wavelength from the visible spectrum and a predetermined wavelength from the near infrared range. The objective imprints on the distal intermediate image a second longitudinal chromatic aberration referred to the predetermined wavelength from the visible spectrum and the predetermined wavelength from the near infrared range. The second longitudinal chromatic aberration has the opposite sign relative to the first longitudinal chromatic aberration, which reduces the longitudinal chromatic aberration caused by the reversal system in the proximal intermediate image.

13 Claims, 5 Drawing Sheets

(51) Int. Cl.
　　*G02B 27/00*　　(2006.01)
　　*A61B 1/055*　　(2006.01)
　　*A61B 1/07*　　(2006.01)
　　*A61B 1/06*　　(2006.01)
　　*A61B 1/00*　　(2006.01)
　　*A61B 1/04*　　(2006.01)
　　*G02B 13/14*　　(2006.01)

(52) U.S. Cl.
　　CPC ...... *A61B 1/00179* (2013.01); *A61B 1/00188* (2013.01); *A61B 1/00195* (2013.01); *A61B 1/04* (2013.01); *A61B 1/042* (2013.01); *A61B 1/043* (2013.01); *A61B 1/055* (2013.01); *A61B 1/0669* (2013.01); *A61B 1/07* (2013.01); *G02B 13/14* (2013.01); *G02B 23/243* (2013.01); *G02B 23/2446* (2013.01); *G02B 23/2453* (2013.01)

(58) Field of Classification Search
　　CPC .............. G02B 13/146; G02B 21/0012; G02B 23/243; G02B 23/2446; G02B 23/2453; G02B 27/0025; G02B 27/005; G02B 27/0062; G02B 3/03; G02B 21/02; A61B 1/00126; A61B 1/00128; A61B 1/00163; A61B 1/00179; A61B 1/00188; A61B 1/00195; A61B 1/04; A61B 1/042; A61B 1/043; A61B 1/0669; A61B 1/07; A61B 1/002; A61B 1/055
　　USPC ................ 359/350, 351, 353, 355–357, 368, 359/434–435, 708–709; 362/574
　　See application file for complete search history.

(56) References Cited

U.S. PATENT DOCUMENTS

| | | | |
|---|---|---|---|
| 6,163,401 | A | 12/2000 | Igarashi |
| 7,586,679 | B2 * | 9/2009 | Lei ..................... G02B 23/2446 359/434 |
| 2016/0174808 | A1 | 6/2016 | Gu |

FOREIGN PATENT DOCUMENTS

| | | | |
|---|---|---|---|
| DE | 102014107456 A1 | 12/2015 | |
| JP | 2013134474 A | 7/2013 | |
| WO | WO-2015135390 A1 * | 9/2015 | ......... A61B 1/00096 |

* cited by examiner

OPTICAL SYSTEM FOR AN ENDOSCOPE

PRIORITY

This application claims the benefit of German Patent Application No. 102016106518.8, filed on Apr. 8, 2016, which is hereby incorporated herein by reference in its entirety.

FIELD

The present invention relates to an optical system for an endoscope, wherein the optical system comprises an objective for imaging an object as a distal intermediate image in a distal intermediate image plane and a reversal system arranged after the objective and comprising at least one reversal stage for projecting the distal intermediate image as a proximal intermediate image into a proximal intermediate image plane.

BACKGROUND

Optical systems for endoscopes are typically designed for radiation from the visible wavelength range in order to be able to realize as good as possible an image for these wavelengths.

However, it is also desirable to be able to carry out imaging with radiation from the near infrared spectrum, since this brings with it an additional benefit in endoscopic diagnostics and in endoscopic surgical techniques. Thus, for example, diseased structures or circulatory disorders can be better recognized and treated by means of fluorescence diagnostics. For this purpose, a medicinal product (e.g. ICG=indocyanine green), which emits a fluorescent signal with a maximum intensity at a wavelength in the range of from 830-840 nm when it is excited with radiation of a predetermined wavelength (e.g. 805 nm), is introduced into the tissue or vascular system to be examined. Thus, for example, images or captures with light from the visible wavelength range and images or captures with radiation from the infrared spectrum can be carried out time-sequentially, which are then represented for the user either individually or in superposition on a display unit. Thus, for example, the fluorescent signal or the corresponding image in the corresponding capture can be marked with light from the visible wave range. It is usual, for example, to stain the fluorescing areas green.

Because conventional optical systems for endoscopes are designed for light from the visible wavelength range, there is a large longitudinal chromatic aberration for light from the visible wavelength range relative to light from the infrared spectrum, which results in it not being possible to carry out a sharp imaging with the light from the near infrared spectrum. The focal position for this light from the near infrared spectrum is spaced apart so far from the focal position for light from the visible wave range that an image sensor which is positioned at the focal position for the light from the visible wavelength range cannot carry out a sharp imaging for light from the near infrared spectrum.

In order now, nevertheless, to be able to carry out the desired sharp imaging for light from the near infrared spectrum, it is possible to focus back and forth either manually or automatically. Furthermore, it is known to provide optical assemblies outside the endoscope, which correct the longitudinal chromatic aberration. Sensors can also be used, which can carry out the imaging with light from the visible wave range and the imaging with light from the near infrared spectrum at different locations. All of these variants are very costly.

Furthermore, it is possible to design the reversal system of the optical system in such a way that the longitudinal chromatic aberration is corrected. However, this results in a very complex reversal system made up of many different optical lenses and materials, which result in large refractive index steps between the material boundary surfaces. Such reversal systems are very costly and also very prone to tolerances.

SUMMARY

Disclosed is an optical system for an endoscope with which addresses the difficulties and drawbacks explained above as completely as possible.

The disclosure includes an optical system for an endoscope, in which the optical system comprises an objective for imaging an object as a distal intermediate image in a distal intermediate image plane and a reversal system arranged after the objective and comprising at least one reversal stage for projecting the distal intermediate image as a proximal intermediate image into a proximal intermediate image plane, wherein the reversal system imprints on the proximal intermediate image a first longitudinal chromatic aberration based on a predetermined wavelength from the visible spectrum and a predetermined wavelength from the near infrared spectrum, wherein the objective imprints on the distal intermediate image a second longitudinal chromatic aberration based on the predetermined wavelength from the visible spectrum and the predetermined wavelength from the near infrared spectrum, and wherein the second longitudinal chromatic aberration has the opposite sign relative to the first longitudinal chromatic aberration in order to reduce the longitudinal chromatic aberration caused by the reversal system in the proximal intermediate image.

Thus, because of its relatively short overall length in comparison with the reversal system, the objective usually hardly contributes to the longitudinal chromatic aberration. The objective is now additionally designed such that it has a very much greater longitudinal chromatic aberration than usual, which moreover is still opposite to the longitudinal chromatic aberration of the reversal system. A correction of the longitudinal chromatic aberration caused by the reversal system is thereby achieved. Furthermore, the optical demands on the reversal system are lower than in a case in which the longitudinal chromatic aberration correction is only carried out by the reversal system, with the result that the reversal system of the optical system can be formed, for example, with few optical elements.

The first longitudinal chromatic aberration can also relate to several predetermined wavelengths (or one or more wavelength ranges) from the visible spectrum (or visible wavelength range) and the predetermined wavelength from the near infrared spectrum or several predetermined wavelengths (or one or more wavelength ranges) from the near infrared spectrum. Furthermore, the first and second longitudinal chromatic aberrations can relate to several wavelengths (or one or more wavelength ranges) from the near infrared spectrum and the predetermined wavelength from the visible spectrum or several wavelengths (or one or more wavelength ranges) from the visible spectrum. It can also be said that the first and second longitudinal chromatic aberrations in each case have a gradient or course, wherein the gradients or courses are opposite such that they become smaller when added together.

All of the curved material boundary surfaces of the objective can be spherically curved. This simplifies the production of the objective.

The reversal system, which can also be referred to as rod lens system, can comprise several reversal stages arranged one behind the other. Preferably, each reversal stage carries out one intermediate projection. The reversal stages are preferably arranged one behind the other in such a way that, through successive intermediate projections, the intermediate image in the distal intermediate image plane is conducted further to the proximal intermediate image plane.

At least one of the reversal stages can comprise two lenses directly joined to each other, the materials of which are chosen such that the refractive indices of the materials differ by not more than 0.3. In particular, at least one of the reversal stages can be formed such that each refractive index step of all lenses which are directly joined to each other of this reversal stage is smaller than or equal to 0.3. The joining of the lenses can be realized e.g. by cementing, gluing or optical contacting.

Through these small refractive index steps, the Fresnel losses are reduced with the result that the transmission can be increased. This is advantageous in particular for the signals from the near infrared spectrum since, as a rule, these are relatively weak.

Here, as a rule, $n_d$ are used as refractive indices and thus the refractive indices for the wavelength of 587.56 nm.

Here, the visible spectrum or the visible wavelength range is, in particular, the wavelength range of 400-700 nm. By near infrared spectrum is meant here, in particular, the range of 710-3000 nm, 710-900 nm or also 780-900 nm.

At least one reversal stage can comprise a lens with an aspherical boundary surface. A good correction of the spherical aberration is thus possible.

The predetermined wavelength from the visible spectrum can, in particular, be a wavelength from the range of 400-700 nm and the predetermined wavelength from the near infrared spectrum can be a wavelength from the range of 710-900 nm.

The several reversal stages of the reversal system can, in particular, be arranged one behind the other such that the intermediate image plane of a reversal stage coincides with the intermediate image plane out of which the following reversal stage projects an intermediate image into the next intermediate image plane of this following reversal stage.

The reversal system can be formed as a symmetrical or as an unsymmetrical rod lens system. In particular, the reversal system can comprise two or more reversal stages, wherein precisely one reversal stage or at least one of the reversal stages is formed as an unsymmetrical reversal stage. In particular, two reversal stages or all reversal stages can be formed as unsymmetrical reversal stages.

Furthermore, a first reversal stage, which lies closest to the distal intermediate image plane, can have a magnification factor greater than 1. A second reversal stage, which lies closest to the first reversal stage, can have a magnification factor smaller than 1. In particular, the first and second reversal stages together can have a magnification factor of 1.

Furthermore, one of the reversal stages can comprise a curved boundary surface facing one of the intermediate image planes, which is aspherically curved. The aspherical curvature can have rotational symmetry. However, it is also possible that the aspherical curvature does not have rotational symmetry and is differently curved in the two principal sections.

At least one rod lens of each reversal system can comprise at least one curved (e.g. spherically or aspherically curved) material boundary surface.

Each reversal stage can, in particular, comprise at least two rod lenses, wherein the rod lenses of a reversal stage can be formed the same or different. If the rod lenses are formed the same, they can be arranged in the same direction as or in opposite directions to each other. At least one of the rod lenses can be constructed from at least two, three or four parts. It is, of course, also possible for it to be constructed from more than four parts. In particular, it can be formed as a cemented component. Furthermore, it is possible for at least one of the rod lenses to be formed in one piece.

At least two reversal stages of the reversal system can be arranged symmetrically with respect to each other.

The optical system can be provided to rigid endoscopes or endoscopes with a rigid endoscope shaft. The optical system can be configured for a forward-viewing endoscope or for an endoscope with an inclined direction of view. Furthermore, it is possible that the optical system is configured such that the direction of view can be changed.

The rod lenses of the reversal stages can have a diameter in the range of from 1 to 7.5 mm, 1 to 6.5 mm and in particular in the range of from 1.7 to 5 mm. The length of a reversal stage can lie in the range of from 30 to 120 mm or in the range of from 40 to 80 mm.

The number of reversal stages can lie in the range of from 1 to 11 or 2 to 11 reversal stages. An odd number of reversal stages is preferred. In particular, one reversal stage, three, five, seven, nine and eleven reversal stages are thus possible. Of course, it is also possible to provide an even number of reversal stages.

The reversal system can in particular have a magnification factor in the range of from 0.5 to 2. Larger or smaller values are likewise possible.

Glass and plastic materials can be used as material for the reversal system and/or the objective.

The predetermined wavelength from the visible spectrum can be 540 nm and the predetermined wavelength from the near infrared spectrum can be 840 nm, wherein the first longitudinal chromatic aberration can lie in the range from 35 to 65 μm (or in the range from 40 to 60 μm) and the second longitudinal chromatic aberration can lie in the range from −4 to −0.5 μm (or in the range from −3.5 to −1 μm).

Further, the ratio of the first longitudinal chromatic aberration to the second longitudinal chromatic aberration (green to infrared) can lie in the range from −55 to −5.

The predetermined wavelength from the visible spectrum can be 540 nm and the predetermined wavelength from the near infrared spectrum can be 840 nm, wherein the ratio of the first longitudinal chromatic aberration to the second longitudinal chromatic aberration (of blue to infrared) can lie in the range from −4 to −1.

The reversal system can comprise a third longitudinal chromatic aberration for the wavelength of 540 nm relative to the wavelength of 460 nm and a fourth longitudinal aberration for the wavelength of 540 nm relative to the wavelength of 640 nm and the objective can comprise a fifth longitudinal chromatic aberration for the wavelength of 540 nm relative to the wavelength of 460 nm and a sixth longitudinal chromatic aberration for the wavelength of 540 nm relative to the wavelength of 640 nm. The ratio of the third longitudinal chromatic aberration to the fourth longitudinal chromatic aberration can lie in the range from −1.1 to −0.8 and the ratio of the fifth longitudinal chromatic aberration to the sixth longitudinal chromatic aberration can lie in the range from −4.5 to −3.

The reversal system and the objective are preferably designed such that the third longitudinal chromatic aberration comprises a negative value and the fifth longitudinal chromatic aberration comprises a positive value.

The objective can comprise a seventh longitudinal chromatic aberration for the wavelength of 460 nm relative to the wavelength of 840 nm and an image angle in the object space. The product of sin(alpha/2) with the seventh longitudinal chromatic aberration can lie in the range from 18 to 26 μm.

In the optical system, the predetermined wavelength from the visible spectrum can be 540 nm and the predetermined wavelength from the near infrared spectrum can be 840 nm and the reversal system can comprise n optical elements. The product of the number n of optical elements and the first longitudinal chromatic aberration can lie in the range from 1500 to 2000 μm.

Further, the objective can imprint on the distal intermediate image such a longitudinal chromatic aberration that the axial position or the focal position for a wavelength of 840 nm lies between the axial positions or focal positions for 540 nm and 640 nm.

In the case of the objective the course of focal positions for the wavelengths 640 nm, 540 nm and 460 nm can be negative. In the case of the reversal system the course of the focal positions can be positive in the wavelength range from 640 nm to 460 nm (preferably a nearly linear course). Further, the course of focus positions can be positive for the wavelengths 460 nm, 540 nm, 640 nm relative to the near infrared spectrum. In other words, the course of the color positions of blue, green and red relative to the near infrared spectrum is positive.

In the case of the objective the extreme value of the focus position as a function of the wavelength can lie in the range from 640 to 680 nm.

The disclosure further includes an endoscope with an optical system according to the disclosure herein.

The endoscope can furthermore comprise an optical unit, such as e.g. an eyepiece, arranged after the reversal system. In addition, the endoscope can comprise a camera connection to which a camera can be detachably secured directly or via a coupler. In addition, the endoscope can comprise an illumination light connection, via which illumination light can be supplied, which is then conducted in the endoscope to the distal end of the shaft of the endoscope in order to illuminate an object located in front of the distal end.

In particular, the endoscope can be formed as an endoscope with a rigid shaft in which the optical system is arranged.

The capturing of light from the visible wavelength range and light from the near infrared are preferably carried out with the endoscope time-sequentially.

The endoscope can include further features known to a person skilled in the art which are necessary for the operation of the endoscope.

It is understood that the features named above and those yet to be explained below can be used not only in the stated combinations but also in other combinations or alone, without departing from the scope of the present invention.

Figure 1:
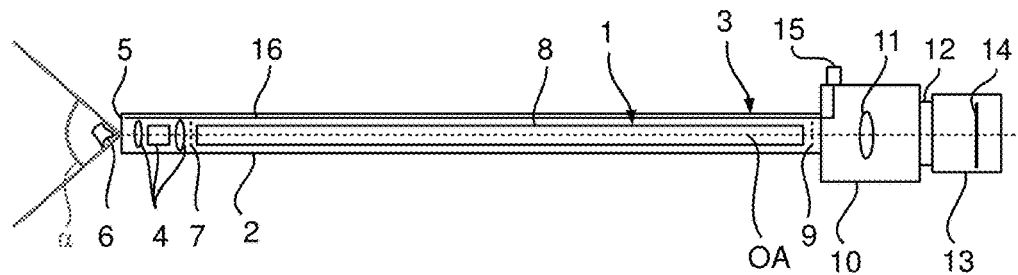
FIG. 1 is a schematic representation of a first embodiment of the optical system in an endoscope.

While the invention is amenable to various modifications and alternative forms, specifics thereof have been shown by way of example in the drawings and will be described in detail. It should be understood, however, that the intention is not to limit the invention to the particular example embodiments described. On the contrary, the invention is to cover all modifications, equivalents, and alternatives falling within the scope of the invention as defined by the appended claims.

DETAILED DESCRIPTION

In the following descriptions, the present invention will be explained with reference to various exemplary embodiments. Nevertheless, these embodiments are not intended to limit the present invention to any specific example, environment, application, or particular implementation described herein. Therefore, descriptions of these example embodiments are only provided for purpose of illustration rather than to limit the present invention.

In the embodiment shown in FIG. 1 the optical system 1 is arranged in a rigid shaft 2 of a schematically represented endoscope 3.

The optical system 1 comprises a schematically represented objective 4, which images an object 6 located in front of a distal end 5 as a distal intermediate image in a distal intermediate image plane 7, and a schematically represented reversal system 8, which projects the distal intermediate image as a proximal intermediate image into a proximal intermediate image plane 9. The objective 4 and the reversal system 8 have a common optical axis OA.

Furthermore, the endoscope 3 comprises a main part 10 in which a further optical system can be arranged, such as e.g. the schematically represented eyepiece 11, as well as a camera connection 12. A camera 13 can be detachably connected to the main part 10 at the camera connection 12, as is represented schematically in FIG. 1. The camera 13 can comprise an optical system (not shown). Furthermore, the camera 13 contains a flat image sensor 14, which is formed, for example, as a CCD sensor or as a CMOS sensor. The camera may not only be connected to the camera connection 12 directly, as is shown in FIG. 1. It is also possible that a coupler (not shown) is connected between the camera connection 12 and the camera 13, which for its part can contain an optical system.

The endoscope 3 shown in FIG. 1 is formed as a forward-viewing endoscope, since an object 6 can be captured with it which is positioned in front of the distal end 5 in the direction in which the endoscope shaft 2 extends. However, it is also possible that the endoscope 3 looks in almost another direction than the direction in which the endoscope shaft 2 extends. This is shown schematically in FIG. 2, wherein here the direction of view is inclined upwards by 45° compared with the direction of extension of the endoscope shaft 2. In the endoscopes according to FIGS. 1 and 2, the reversal system 8 is in each case formed the same. Only the objective 4 differs in that the desired deflection, where necessary, takes place in the objective, as will be described in detail in the following.

Furthermore, the endoscope can comprise e.g. on the main part 10 an illumination connection 15, via which the desired illumination radiation can be supplied to the endoscope 3. The illumination connection 15 is connected to a schematically drawn in light guide 16, which extends to the distal end 5 of the endoscope 3 and emits the guided radiation for the illumination of the object 6.

Figure 2:
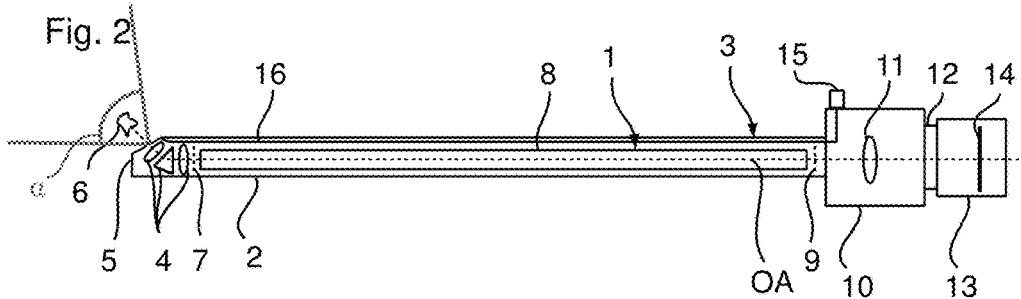
FIG. 2 is a schematic representation of a second embodiment of the optical system in an endoscope.
Figure 3:
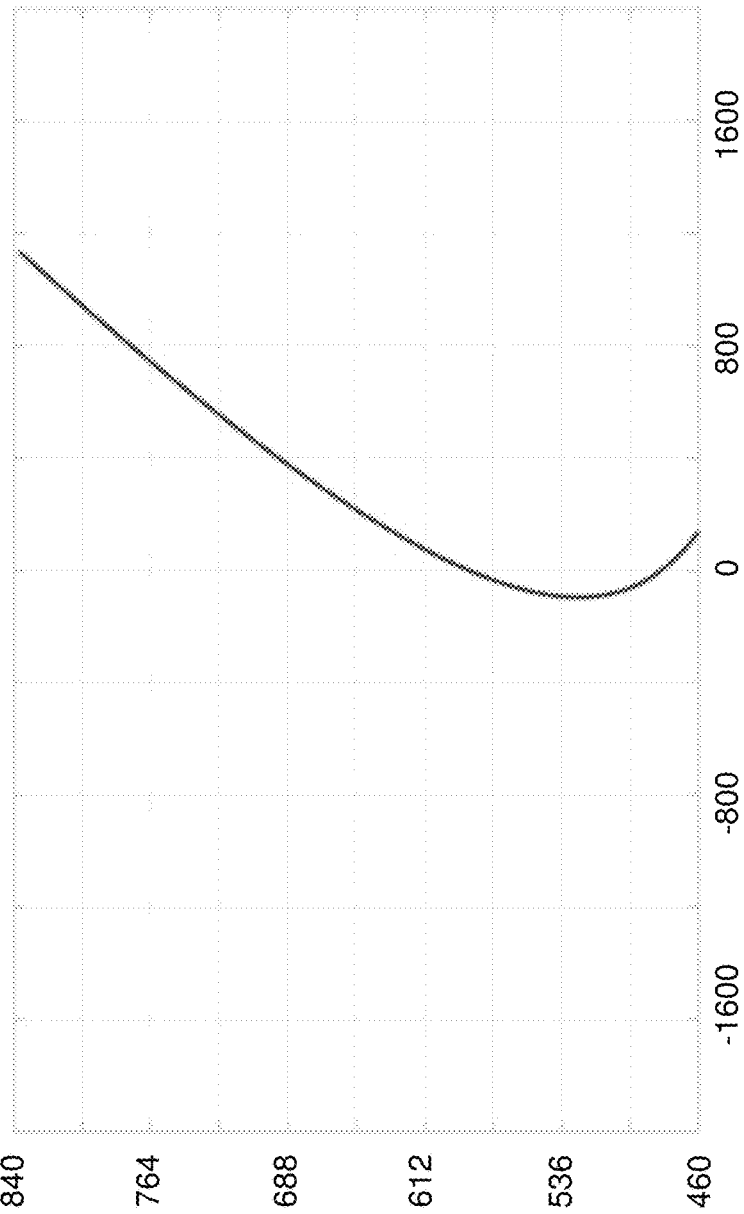
FIG. 3 is a representation of the dependence of the focal position on the wavelength for a conventional optical system.

In the operation of the endoscope 3, the object 6 to be imaged is illuminated with the radiation from the light guide 16 and the illuminated object 6 is imaged via the optical system 1 in the proximal intermediate image plane 9 and there in the plane of the image sensor 14 by means of the eyepiece 11, such that the image sensor 14 can capture a sharp image of the object 6. Known endoscopes are usually designed for the wavelength range of from approx. 400 to 700 nm, which is visible to the human eye. The wavelength-dependent longitudinal chromatic aberration is to be as small as possible for the visible wave range. In FIG. 3, the focal position produced in a conventional endoscope is plotted along the x-axis in µm as a function of the wavelength along the y-axis in nm. A focal position of 0 µm means that the location of the sharpest image coincides with the plane in which the image sensor 14 lies. A focal position of greater than 0 µm means that the location of the sharpest image is behind (and thus further to the right in FIGS. 1 and 2) the plane in which the image sensor 14 lies. Correspondingly, a negative focal position is a deviation from the optimal focal position in the direction towards the distal end 5. As can be learned from this representation, deviations in the range of from approx. −100 µm to 400 µm are in the range of from 460 to 700 nm. This is still acceptable for a sufficiently good imaging by means of the sensor 14.

However, in FIG. 3, the focal positions are also shown for wavelengths of greater than 700 nm and in particular for the range of from 700 to 840 nm. This range from 700 nm and, for example, from 700 to 900 nm or also from 780 to 3000 nm, is referred to as the near infrared spectrum and is of increasing interest for endoscopy, since e.g. in addition to imaging with light from the visible wavelength range, fluorescence diagnostics can also be carried out. For example, a fluorescent substance, such as e.g. ICG (indocyanine green), can be injected into tissue to be examined or a vascular system to be examined, which substance emits a fluorescent signal with longer wavelengths, the wavelengths of which are e.g. 830 to 840 nm, when excited with light of a wavelength of approx. 805 nm. It is therefore desired also to be able to capture an image with radiation from the near infrared spectrum by means of the camera 13. As can be learned from the representation in FIG. 3, however, the longitudinal chromatic aberration based e.g. on the wavelength of 540 nm and the wavelength of 840 nm (and thus the difference of the focal positions for these two wavelengths) is about 1200 µm. In the case of the wavelengths 460 nm and 840 nm, the longitudinal chromatic aberration is about 1000 µm. This results in it not being possible to carry out a sharp imaging with the fluorescent signals.

The longitudinal chromatic aberration described is mainly produced by the reversal system, since, because of the necessary length of the shaft 2, many rod lenses with different materials are necessary, which all contribute to the longitudinal chromatic aberration. The optical system 1 is therefore designed such that the longitudinal chromatic aberration caused by the reversal system 8 is reduced as much as possible by an opposite longitudinal chromatic aberration of the objective 4. As a rule, the objective 4 hardly contributes to the longitudinal chromatic aberration because of the very much shorter extension in comparison with the reversal system 8. The objective 4 is now designed such that it has a very much larger longitudinal chromatic aberration than usual, which, however, is opposite to the longitudinal chromatic aberration of the reversal system 8, with the result that the resulting longitudinal chromatic aberration in the intermediate image in the proximal intermediate image plane 9 is reduced to the case in which the objective would cause no longitudinal chromatic aberration at all and the longitudinal chromatic aberration would only be caused by the reversal system.

Figure 4:
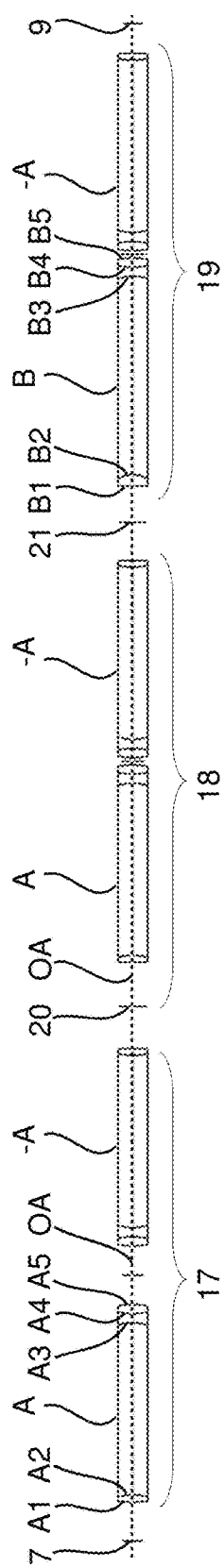
FIG. 4 is a schematic representation of the structure of the reversal system of the optical system.

In the optical system 1 according to the invention, the reversal system 8, as is shown in FIG. 4, is formed from three reversal stages 17, 18, 19 arranged one behind the other, which in each case project an intermediate image into a next intermediate image plane. The first reversal stage 17 thus projects the intermediate image lying in the distal intermediate image plane 7 into a second intermediate image plane 20. The second reversal stage 18 projects the intermediate image lying in the second intermediate image plane 20 into a third intermediate image plane 21. The third reversal stage 19 projects the intermediate image from the third intermediate image plane 21 into the proximal intermediate image plane 9.

The three reversal stages 17-19 are thus arranged one behind the other such that an intermediate image lying in the distal intermediate image plane 7 is projected (via in each case the next intermediate image plane 20 and 21) into the proximal intermediate image plane 9. Since each reversal stage 17-19 during the projection of the intermediate image produces a reversed intermediate image and an odd number of reversal stages 17-19 are provided, the intermediate image of the object 6 lying in the distal intermediate image plane 7 is projected into the proximal intermediate image plane 9 as a reversed intermediate image.

The two reversal stages 17 and 18 comprise in each case two rod lenses of type A. The reversal stage 19 comprises a rod lens of type A and a rod lens of type B. All rod lenses of type A have spherical radii and are constructed identically. The rod lens labelled with—A in FIG. 4 is identical to the rod lens of type A, merely mounted the other way around. The rod lenses of type A comprise the boundary surfaces A1 (positively spherically curved), A2 (negatively spherically curved), A3 (negatively spherically curved), A4 (positively spherically curved) and A5 (negatively spherically curved). The material between the surfaces A1 and A2 has a refractive index $n_d=1.8$ and an Abbe number $v_d=29.9$. The material between the boundary surfaces A2 and A3 has a refractive index $n_d=1.5182$ and an Abbe number $v_d=58.9$. The material between the boundary surfaces A3 and A4 has a refractive index of $n_d=1.6377$ and an Abbe number of $v_d$=42.4. The material between the boundary surfaces A4 and A5 has a refractive index of $n_d$=1.65 and an Abbe number of $v_d$=50.9.

The rod lens of type B comprises the boundary surfaces B1 (positively aspherically curved), B2 (negatively spherically curved), B3 (negatively spherically curved), B4 (positively spherically curved) and B5 (negatively spherically curved). The material between the boundary surfaces B1 and B2 has a refractive index $n_d$=1.75 and an Abbe number of $v_d$=45.4. The material between the boundary surfaces B2 and B3 has a refractive index of $n_d$=1.523 and an Abbe number of $v_d$=59.5. The material between the boundary surfaces B3 and B4 has a refractive index $n_d$=1.6377 and an Abbe number $v_d$=42.4. The material between the boundary surfaces B4 and B5 has a refractive index of $n_d$=1.65 and an Abbe number of $v_d$=50.9.

Figure 5:
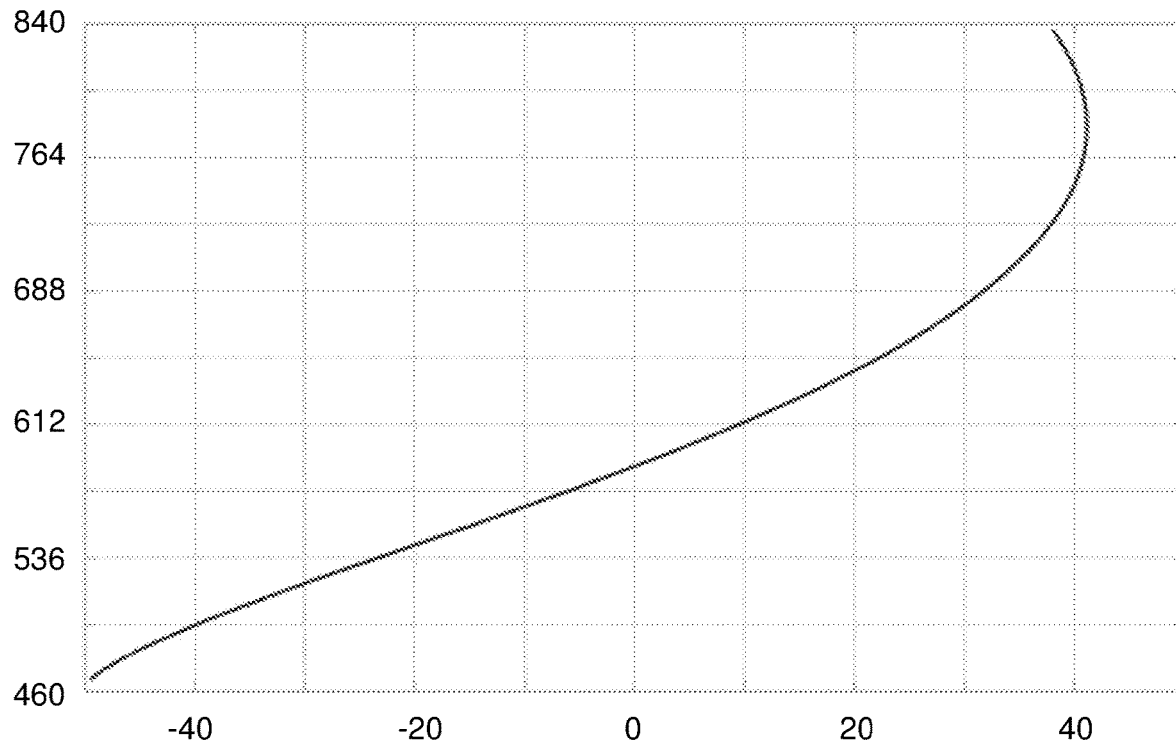
FIG. 5 is a schematic representation of the focal position caused by the reversal system according to FIG. 4 as a function of the wavelength.

A reversal system 6 formed in this way has a longitudinal chromatic aberration behaviour as is shown in FIG. 5. In FIG. 5, in the same way as in FIG. 3, the focal position is plotted along the x-axis in μm and the wavelength is plotted along the y-axis in nm. From this representation in FIG. 5 it can be learned that the longitudinal chromatic aberration for a first predetermined wavelength of 540 nm from the visible wavelength range in relation to a second predetermined wavelength of 840 nm from the near infrared spectrum is approx. 59.05 μm. For the wavelengths 460 nm and 840 nm, the longitudinal chromatic aberration is approx. 88.08 μm. The longitudinal chromatic aberration behaviour can be described as a positive longitudinal chromatic aberration.

Figure 6:
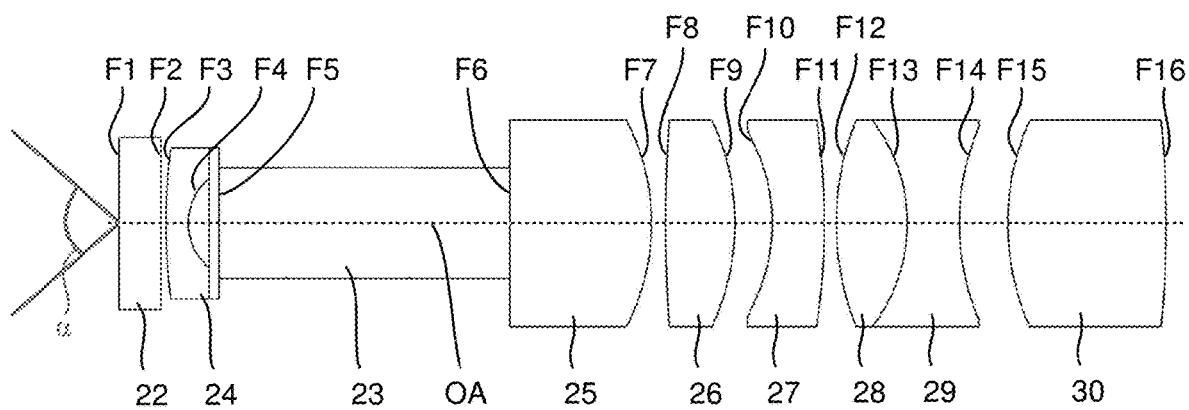
FIG. 6 is a schematic representation of the optical structure of the objective of the optical system according to certain embodiments.

The objective 4 has the structure shown in FIG. 6 with an optical flat 22, a prism 23 and lenses 24-30. In the representation in FIG. 6, the prism 23 is represented as an extended glass block, which, in the formation of the optical system for a forward-viewing endoscope, as is shown in FIG. 1, is realized as the glass block shown. In the case of the implementation of the optical system 1 for an inclined direction of view, as is shown in FIG. 2, the prism 23 is then actually formed as a prism. The representation chosen in FIG. 6 serves only for simplification of the representation, since the description of the longitudinal chromatic aberration depends on the glass paths as well as on the curved boundary surfaces.

The curvature properties and materials used are indicated in the following table (Table 1) for the surfaces F1-F16 of the objective 4, wherein the specification of the refractive index $n_d$ and of the Abbe number $v_d$ for a surface means that this material is present between the surface in the line of which the specifications are and the next following surface.

TABLE 1

| Surface | Curvature | Refractive index $n_d$ | Abbe number $v_d$ |
| --- | --- | --- | --- |
| F1 | flat | 1.768 | 72.2 |
| F2 | flat | | |
| F3 | positive spherical | 1.892 | 37.1 |
| F4 | positive spherical | | |
| F5 | flat | 1.835 | 42.7 |
| F6 | flat | 1.8502 | 32.2 |
| F7 | negative spherical | | |
| F8 | positive spherical | 1.529 | 77 |
| F9 | negative spherical | | |
| F10 | negative spherical | 1.855 | 24.8 |
| F11 | negative spherical | | |
| F12 | positive spherical | 1.603 | 65.4 |
| F13 | negative spherical | 1.6377 | 42.4 |
| F14 | positive spherical | | |
| F15 | positive spherical | 1.529 | 77 |
| F16 | negative spherical | | |

Figure 7:
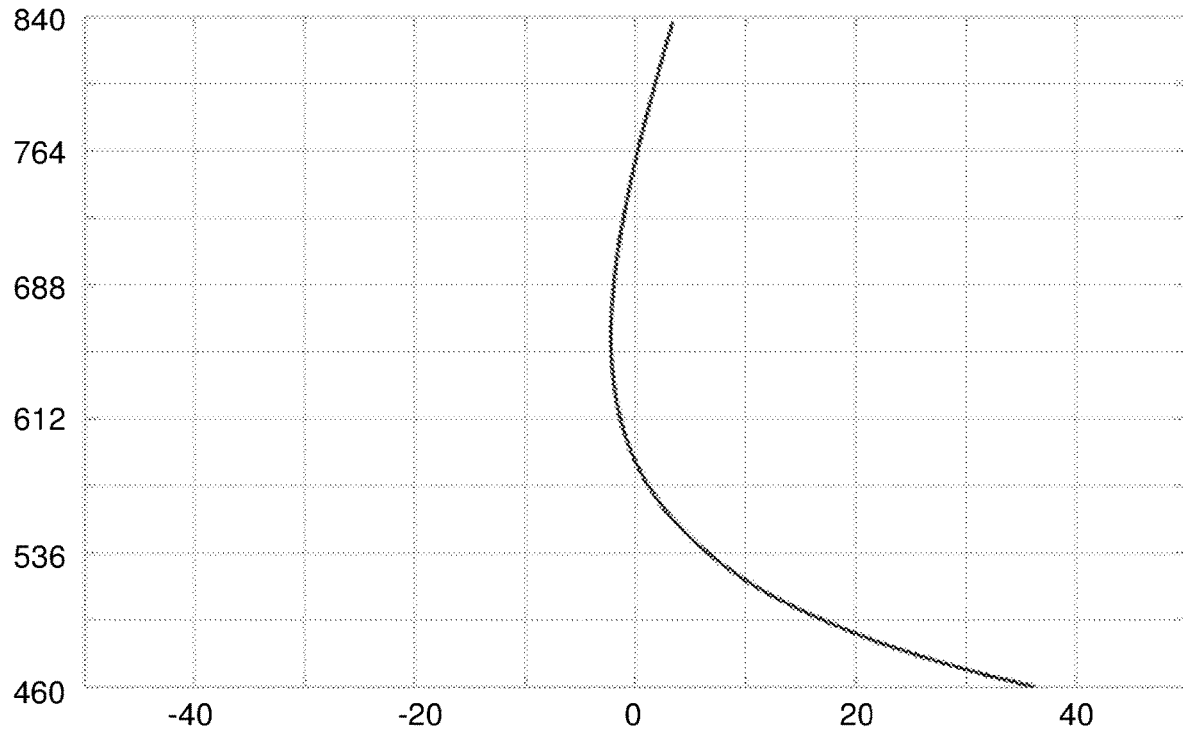
FIG. 7 is a representation of the focal position caused by the objective as a function of the wavelength.
Figure 8:
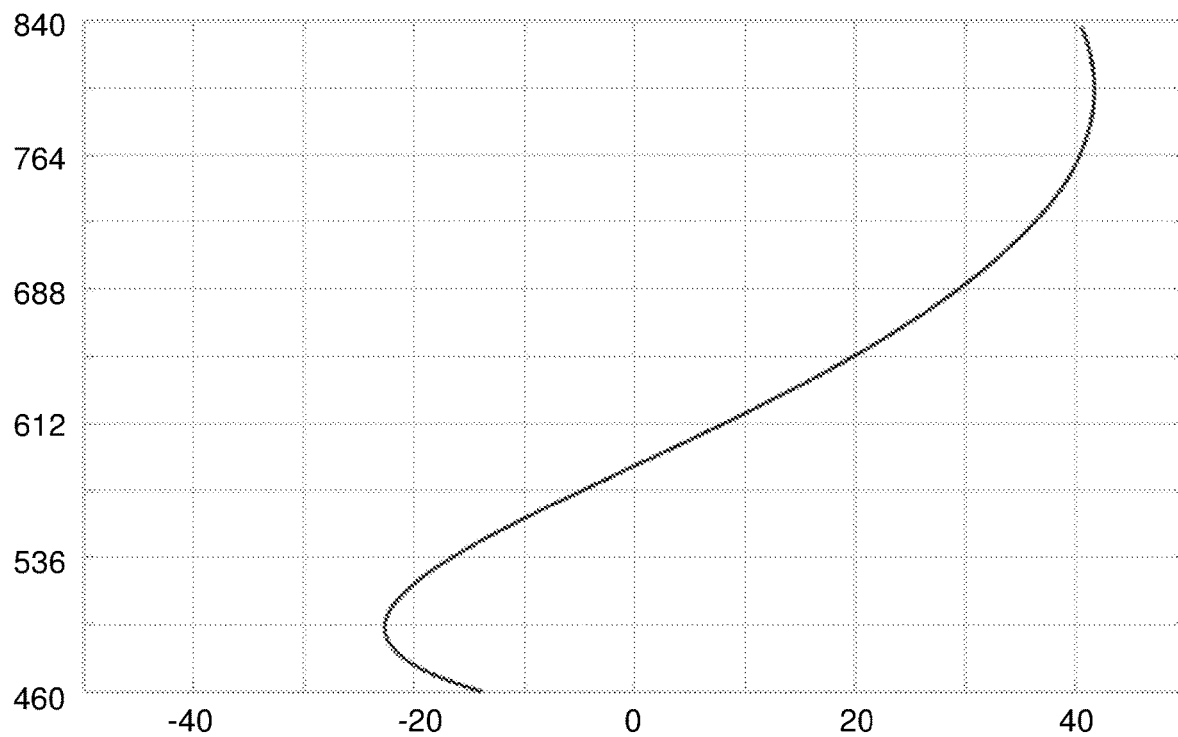
FIG. 8 is a schematic representation of the focal position caused by the optical system as a function of the wavelength.

The longitudinal chromatic aberration caused by the objective 4 is represented in FIG. 7 in the same way as in FIG. 5. The objective 4 was designed such that there is an essentially negative longitudinal chromatic aberration. Thus, for the wavelengths 540 nm and 840 nm, the longitudinal chromatic aberration is −2.3 μm. For the wavelengths 460 nm and 840 nm it is −32.7 μm. The longitudinal chromatic aberration imprinted by the objective 4 and the reversal system 8 as a whole during the projection from the distal intermediate image plane 7 into the proximal intermediate image plane 9 is shown in FIG. 8. Because of the opposite longitudinal chromatic aberrations of objective 4 and reversal system 8, the resulting longitudinal chromatic aberration is smaller than that of the reversal system 8 alone. Thus, for the wavelengths 540 and 840 nm, the longitudinal chromatic aberration is approx. 55.61 μm and for the wavelengths 460 and 840 nm approx. 54.05 μm. Because of this extremely small longitudinal chromatic aberration, sharp captures are possible without problems with light from the visible wavelength spectrum and with light from the infrared spectrum.

Figure 9:
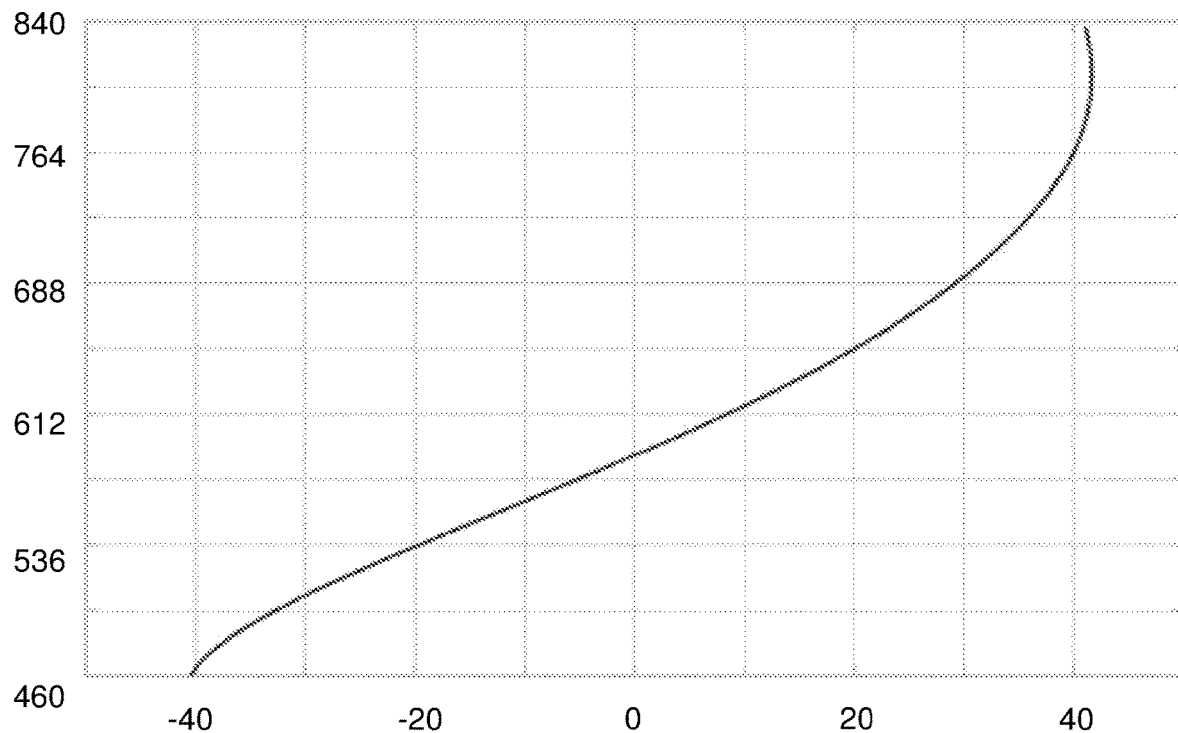
FIG. 9 is a schematic representation of the focal position caused by a reversal system of a known endoscope as a function of the wavelength.
Figure 10:
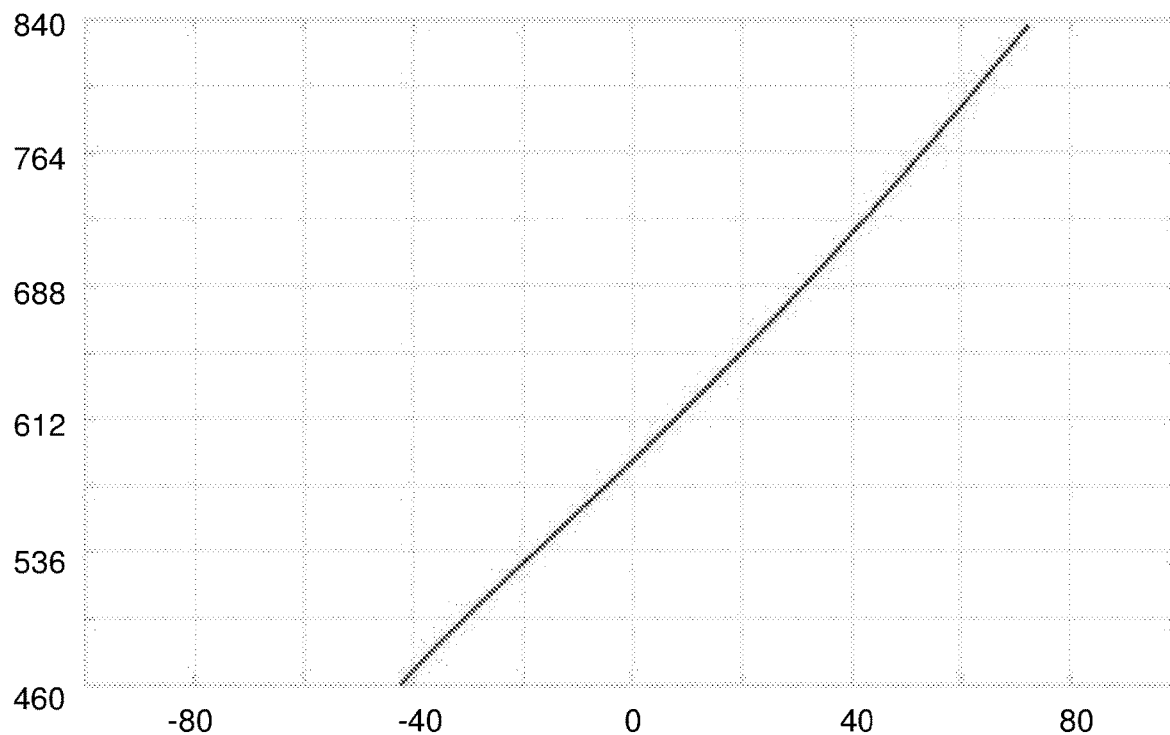
FIG. 10 is a schematic representation of the focal position caused by an objective of a known optical system as a function of the wavelength.
Figure 11:
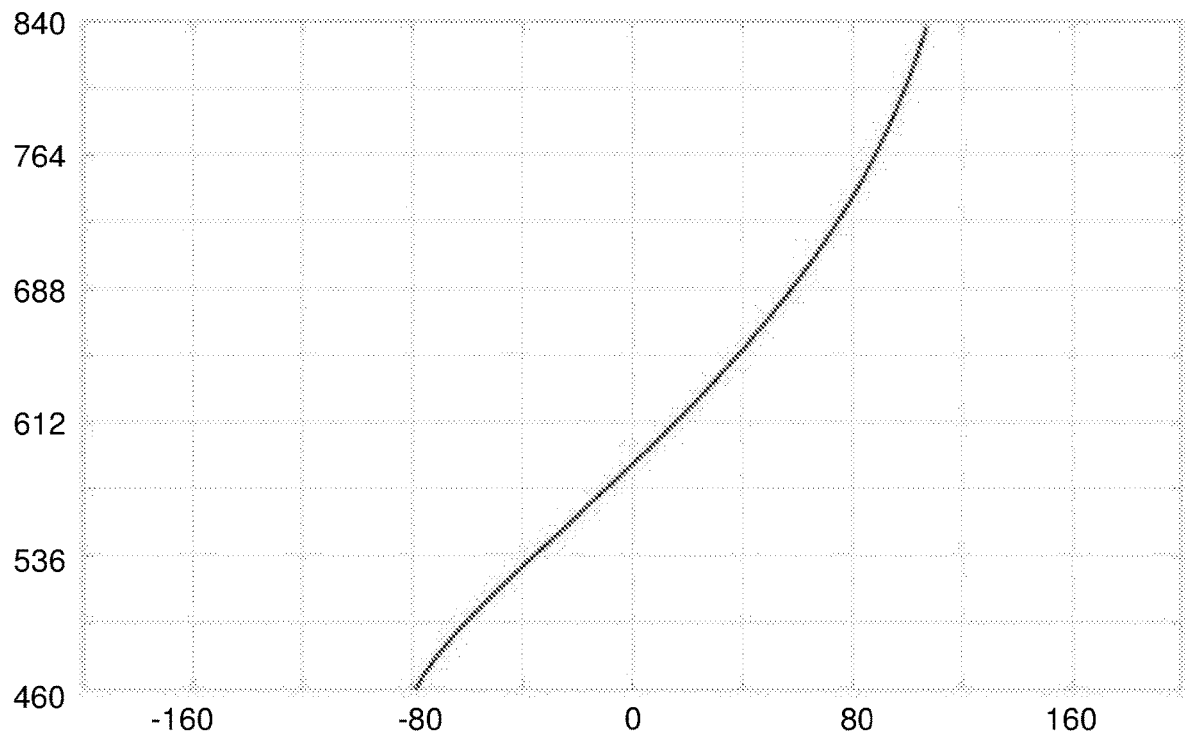
FIG. 11 is a schematic representation of the focal position of a known optical system as a function of the wavelength.

In FIGS. 9-11, the longitudinal chromatic aberration of a reversal system (FIG. 9), the longitudinal chromatic aberration of an objective (FIG. 10) and the resulting longitudinal chromatic aberration of objective and reversal system (FIG. 11) of a known comparison endoscope (which also comprises an optical system made up of objective and reversal system in a rigid endoscope shaft) are shown in the same way as in FIGS. 5-8. The comparison endoscope was designed with respect to as small as possible a longitudinal chromatic aberration of the reversal system. This is also slightly smaller than that of the reversal system 8 of the optical system according to the invention. Thus, for 540 and 840 nm, the longitudinal chromatic aberration of the reversal system of the comparison endoscope is approx. 59 μm and for 460 and 840 nm approx. 82.1 μm. This is achieved through the use of many different glasses, since the reversal system of the comparison endoscope comprises three reversal stages of two rod lenses with, in each case, 4-5 elements, with the result that in total 27 elements are provided. Furthermore, the refractive index steps between the different materials are greater than 0.5.

The objective of the comparison endoscope has the positive longitudinal chromatic aberration according to FIG. 10. Thus, for 540 and 840 nm, the longitudinal chromatic aberration is approx. 88.7 μm and for 460 and 840 nm approx. 115.5 μm. Although this is a small longitudinal chromatic aberration, it is positive with the result that the resulting longitudinal chromatic aberration, as is shown in FIG. 11, for 540-840 nm is approx. 140 μm and for 460-840 nm is approx. 186.7 μm. The resulting longitudinal chromatic aberration is thus considerably larger than in the case of the optical system according to the invention.

In addition, the use of more optical elements in the reversal system and of materials with refractive index steps of greater than 0.5 in the reversal system results in larger Fresnel losses occurring in comparison with the reversal system 8 according to the invention, in which the refractive index steps are not greater than 0.3. Because of the smaller refractive index steps and the lower number of lenses in the reversal system 8 according to the invention, the transmission of the optical system 1 according to the invention is considerably higher. Thus, the transmission in the optical system 1 according to the invention for the wavelengths 460 nm, 540 nm, 588 nm, 640 nm, 656 nm and 840 nm is 0.69, 0.77, 0.78, 0.77, 0.76 and 0.78, respectively. This gives a total transmission of 0.75. In the case of the optical system of the known endoscope, in contrast, the transmission for the same wavelengths is only 0.60, 0.71, 0.72, 0.72, 0.72 and 0.74. The total transmission is then 0.68. Thus, in the case of the optical system 1 according to the invention, there is a 16% greater brightness for blue (640 nm), a 9% greater brightness for green (540 nm) and a 5% greater brightness for near infrared 840 nm. Moreover, because of the higher transmission of blue, the image is whiter, which brings about a better image impression.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products. Moreover, features or aspects of various example embodiments may be mixed and matched (even if such combination is not explicitly described herein) without departing from the scope of the invention.

What is claimed is:

1. An optical system for an endoscope, comprising:
an objective configured to image an object as a distal intermediate image in a distal intermediate image plane; and
a reversal system arranged after the objective, including at least one reversal stage configured to project the distal intermediate image as a proximal intermediate image into a proximal intermediate image plane,
wherein the reversal system is configured to imprint on the proximal intermediate image a first longitudinal chromatic aberration from a predetermined wavelength from a visible spectrum to a predetermined wavelength from a near infrared spectrum,
wherein the objective is configured to imprint on the distal intermediate image a second longitudinal chromatic aberration from the predetermined wavelength from the visible spectrum to the predetermined wavelength from the near infrared spectrum,
wherein the second longitudinal chromatic aberration has a sign that is opposite relative to a sign of the first longitudinal chromatic aberration such that the first longitudinal chromatic aberration caused by the reversal system in the proximal intermediate image is reduced,
wherein at least one reversal stage comprises two lenses directly joined to each other, each of the two lenses comprising a material chosen such that a refractive index of each of the respective materials differs by not more than 0.3,
wherein the reversal system comprises a third longitudinal chromatic aberration for a wavelength of 540 nm relative to a wavelength of 460 nm and a fourth longitudinal chromatic aberration for a wavelength of 540 nm relative to a wavelength of 640 nm, and
wherein the objective comprises a fifth longitudinal chromatic aberration for the wavelength of 540 nm relative to the wavelength of 460 nm and a sixth longitudinal chromatic aberration for the wavelength of 540 nm relative to the wavelength of 640 nm, and
wherein a ratio of the third longitudinal chromatic aberration to the fourth longitudinal chromatic aberration lies in the range from −1.1 to −0.8 and a ratio of the fifth longitudinal chromatic aberration to the sixth longitudinal chromatic aberration lies in the range from −4.5 to −3.

2. The optical system according to claim 1, wherein all curved material boundary surfaces of the objective are spherically curved.

3. The optical system according to claim 1, wherein the reversal system comprises several reversal stages arranged one behind the other.

4. The optical system according to claim 1, wherein at least one reversal stage comprises a lens with an aspherical boundary surface.

5. The optical system according to claim 1, wherein the predetermined wavelength from the visible spectrum is in a range of 400-700 nm and the predetermined wavelength from the near infrared spectrum is in a range of 710-900 nm.

6. The optical system according to claim 1,
wherein the predetermined wavelength from the visible spectrum is 540 nm and the predetermined wavelength from the near infrared spectrum is 840 nm, and
wherein the first longitudinal chromatic aberration lies in a range from 35 to 65 μm and the second longitudinal chromatic aberration lies in a range from −4 to −0.5 μm.

7. The optical system for an endoscope according to claim 1,
wherein the predetermined wavelength from the visible spectrum is 460 nm and the predetermined wavelength from the near infrared spectrum is 840 nm, and
wherein a ratio of the first longitudinal chromatic aberration to the second longitudinal chromatic aberration lies in a range from −4 to −1.

8. The optical system according to claim 1,
wherein the objective comprises a seventh longitudinal chromatic aberration for the wavelength of 460 nm relative to the wavelength of 840 nm and an image angle alpha in an object space, and
wherein a product of sin(alpha/2) and the seventh longitudinal chromatic aberration lies in a range from 18 to 26 μm.

9. The optical system according to claim 1,
wherein the predetermined wavelength from the visible spectrum is 540 nm and the predetermined wavelength from the near infrared spectrum is 840 nm and the reversal system comprises n optical elements,
wherein a product of the number n of optical elements and the first longitudinal chromatic aberration of the reversal system lies in a range from 1500 to 2000 μm.

10. The optical system according to claim 1, wherein the objective is configured to imprint on the distal intermediate image such a longitudinal chromatic aberration that a focus position of a wavelength of 840 nm lies between a focus position for 540 nm and a focus position for 640 nm.

11. An endoscope, comprising an optical system according to claim 1.

12. An optical system for an endoscope, comprising:
an objective configured to image an object as a distal intermediate image in a distal intermediate image plane; and
a reversal system arranged after the objective, including at least one reversal stage configured to project the distal intermediate image as a proximal intermediate image into a proximal intermediate image plane,
wherein the reversal system is configured to imprint on the proximal intermediate image a first longitudinal chromatic aberration from a predetermined wavelength from a visible spectrum to a predetermined wavelength from a near infrared spectrum, wherein the objective is configured to imprint on the distal intermediate image a second longitudinal chromatic aberration from the predetermined wavelength from the visible spectrum to the predetermined wavelength from the near infrared spectrum, wherein the second longitudinal chromatic aberration has a sign that is opposite relative to a sign of the first longitudinal chromatic aberration such that the first longitudinal chromatic aberration caused by the reversal system in the proximal intermediate image is reduced, wherein the predetermined wavelength from the visible spectrum is 540 nm and the predetermined wavelength from the near infrared spectrum is 840 nm, and wherein the first longitudinal chromatic aberration lies in a range from 35 to 65 µm and the second longitudinal chromatic aberration lies in a range from −4 to −0.5 µm.

13. An optical system for an endoscope, comprising:
an objective configured to image an object as a distal intermediate image in a distal intermediate image plane; and
a reversal system arranged after the objective, including at least one reversal stage configured to project the distal intermediate image as a proximal intermediate image into a proximal intermediate image plane,
wherein the reversal system is configured to imprint on the proximal intermediate image a first longitudinal chromatic aberration from a predetermined wavelength from a visible spectrum to a predetermined wavelength from a near infrared spectrum,
wherein the objective is configured to imprint on the distal intermediate image a second longitudinal chromatic aberration from the predetermined wavelength from the visible spectrum to the predetermined wavelength from the near infrared spectrum,
wherein the second longitudinal chromatic aberration has a sign that is opposite relative to a sign of the first longitudinal chromatic aberration such that the first longitudinal chromatic aberration caused by the reversal system in the proximal intermediate image is reduced,
wherein at least one reversal stage comprises two lenses directly joined to each other, each of the two lenses comprising a material chosen such that a refractive index of each of the respective materials differs by not more than 0.3,
wherein the objective comprises a seventh longitudinal chromatic aberration for a wavelength of 460 nm relative to a wavelength of 840 nm and an image angle alpha in an object space, and
wherein a product of sin(alpha/2) and the seventh longitudinal chromatic aberration lies in a range from 18 to 26 µm.

* * * * *